United States Patent
Paterson et al.

(10) Patent No.: US 7,766,905 B2
(45) Date of Patent: Aug. 3, 2010

(54) METHOD AND SYSTEM FOR CONTINUITY TESTING OF MEDICAL ELECTRODES

(75) Inventors: William G. Paterson, Longmont, CO (US); Derek M. Blaha, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 553 days.

(21) Appl. No.: 11/051,075

(22) Filed: Feb. 4, 2005

(65) Prior Publication Data

US 2005/0182398 A1  Aug. 18, 2005

Related U.S. Application Data

(60) Provisional application No. 60/543,877, filed on Feb. 12, 2004.

(51) Int. Cl.
*A61B 18/12* (2006.01)
(52) U.S. Cl. ...................................................... 606/34
(58) Field of Classification Search ............. 606/32–52
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |

(Continued)

FOREIGN PATENT DOCUMENTS

DE 179607 3/1905

(Continued)

OTHER PUBLICATIONS

International Search Report EP 06000708.5 dated Apr. 21, 2006.

(Continued)

*Primary Examiner*—Michael Peffley
*Assistant Examiner*—Ronald Hupczey, Jr.

(57) ABSTRACT

An electrosurgical generator is provided which includes a continuity test circuit assembly for testing electrical continuity through an electrode of an electrosurgical instrument. The continuity test circuit assembly includes a test power source providing electrical test energy to a first conductor which is in electrical communication with the electrode and the electrosurgical generator and to at least one second conductor which is coupled to the first conductor for providing a path for current to flow between the first conductor and the at least one second conductor for establishing a test path through which the test energy flows between the first conductor and at least one conductor of the at least one second conductor. The continuity test circuit assembly further includes energy detection circuitry positioned along the test path for detecting the flow of the test energy through the test path for determining electrical continuity through the electrode.

20 Claims, 4 Drawing Sheets

U.S. PATENT DOCUMENTS

| | | |
|---|---|---|
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A * | 2/1972 | Bolduc ........................ 607/152 |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |

| Patent No. | Kind | Date | Inventor |
|---|---|---|---|
| 4,754,757 | A | 7/1988 | Feucht |
| 4,788,634 | A | 11/1988 | Schlecht et al. |
| 4,805,621 | A | 2/1989 | Heinze et al. |
| 4,818,954 | A | 4/1989 | Flachenecker et al. |
| 4,827,911 | A | 5/1989 | Broadwin et al. |
| 4,827,927 | A | 5/1989 | Newton |
| 4,832,024 | A | 5/1989 | Boussignac et al. |
| 4,848,335 | A | 7/1989 | Manes |
| 4,848,355 | A | 7/1989 | Nakamura et al. |
| 4,860,745 | A | 8/1989 | Farin et al. |
| 4,862,889 | A | 9/1989 | Feucht |
| 4,880,719 | A | 11/1989 | Murofushi et al. |
| 4,887,199 | A | 12/1989 | Whittle |
| 4,890,610 | A | 1/1990 | Kirwan et al. |
| 4,903,696 | A | 2/1990 | Stasz et al. |
| 4,907,589 | A | 3/1990 | Cosman |
| 4,922,210 | A | 5/1990 | Flachenecker et al. |
| 4,931,047 | A | 6/1990 | Broadwin et al. |
| 4,931,717 | A | 6/1990 | Gray et al. |
| 4,938,761 | A | 7/1990 | Ensslin |
| 4,942,313 | A | 7/1990 | Kinzel |
| 4,959,606 | A | 9/1990 | Forge |
| 4,961,047 | A | 10/1990 | Carder |
| 4,961,435 | A | 10/1990 | Kitagawa et al. |
| 4,966,597 | A | 10/1990 | Cosman |
| RE33,420 | E | 11/1990 | Sussman |
| 4,969,885 | A | 11/1990 | Farin |
| 4,992,719 | A | 2/1991 | Harvey |
| 4,993,430 | A | 2/1991 | Shimoyama et al. |
| 4,995,877 | A | 2/1991 | Ams et al. |
| 5,015,227 | A | 5/1991 | Broadwin et al. |
| 5,019,176 | A | 5/1991 | Brandhorst, Jr. |
| 5,024,668 | A | 6/1991 | Peters et al. |
| 5,029,588 | A | 7/1991 | Yock et al. |
| 5,087,257 | A | 2/1992 | Farin |
| 5,099,840 | A | 3/1992 | Goble et al. |
| 5,103,804 | A | 4/1992 | Abele et al. |
| 5,108,389 | A | 4/1992 | Cosmescu |
| 5,108,391 | A | 4/1992 | Flachenecker |
| 5,122,137 | A | 6/1992 | Lennox |
| 5,133,711 | A | 7/1992 | Hagen |
| 5,151,102 | A | 9/1992 | Kamiyama et al. |
| 5,152,762 | A | 10/1992 | McElhenney |
| 5,157,603 | A | 10/1992 | Scheller et al. |
| 5,160,334 | A | 11/1992 | Billings et al. |
| 5,162,217 | A | 11/1992 | Hartman |
| 5,167,658 | A | 12/1992 | Ensslin |
| 5,190,517 | A | 3/1993 | Zieve et al. |
| 5,196,008 | A | 3/1993 | Kuenecke |
| 5,196,009 | A | 3/1993 | Kirwan, Jr. |
| 5,201,900 | A | 4/1993 | Nardella |
| 5,207,691 | A | 5/1993 | Nardella |
| 5,230,623 | A | 7/1993 | Guthrie et al. |
| 5,233,515 | A | 8/1993 | Cosman |
| 5,249,121 | A | 9/1993 | Baum et al. |
| 5,254,117 | A | 10/1993 | Rigby et al. |
| RE34,432 | E | 11/1993 | Bertrand |
| 5,267,994 | A | 12/1993 | Gentelia et al. |
| 5,267,997 | A | 12/1993 | Farin et al. |
| 5,281,213 | A | 1/1994 | Milder et al. |
| 5,300,068 | A | 4/1994 | Rosar et al. |
| 5,300,070 | A | 4/1994 | Gentelia |
| 5,318,563 | A | 6/1994 | Malis et al. |
| 5,323,778 | A | 6/1994 | Kandarpa et al. |
| 5,324,283 | A | 6/1994 | Heckele |
| 5,330,518 | A | 7/1994 | Neilson et al. |
| 5,334,183 | A | 8/1994 | Wuchinich |
| 5,334,193 | A | 8/1994 | Nardella |
| 5,341,807 | A | 8/1994 | Nardella |
| 5,342,356 | A | 8/1994 | Ellman et al. |
| 5,342,357 | A | 8/1994 | Nardella |
| 5,342,409 | A | 8/1994 | Mullett |
| 5,348,554 | A | 9/1994 | Imran et al. |
| 5,370,645 | A | 12/1994 | Klicek et al. |
| 5,370,672 | A | 12/1994 | Fowler et al. |
| 5,370,675 | A | 12/1994 | Edwards et al. |
| 5,372,596 | A | 12/1994 | Klicek et al. |
| 5,383,874 | A | 1/1995 | Jackson et al. |
| 5,383,876 | A | 1/1995 | Nardella |
| 5,383,917 | A | 1/1995 | Desai et al. |
| 5,385,148 | A | 1/1995 | Lesh et al. |
| 5,396,062 | A | 3/1995 | Eisentraut et al. |
| 5,400,267 | A | 3/1995 | Denen et al. |
| 5,403,311 | A | 4/1995 | Abele et al. |
| 5,403,312 | A | 4/1995 | Yates et al. |
| 5,409,000 | A | 4/1995 | Imran |
| 5,409,006 | A | 4/1995 | Buchholtz et al. |
| 5,409,485 | A | 4/1995 | Suda |
| 5,413,573 | A | 5/1995 | Koivukangas |
| 5,414,238 | A | 5/1995 | Steigerwald et al. |
| 5,417,719 | A | 5/1995 | Hull et al. |
| 5,422,567 | A | 6/1995 | Matsunaga |
| 5,423,808 | A | 6/1995 | Edwards et al. |
| 5,423,809 | A | 6/1995 | Klicek |
| 5,423,810 | A | 6/1995 | Goble et al. |
| 5,425,704 | A | 6/1995 | Sakurai et al. |
| 5,430,434 | A | 7/1995 | Lederer et al. |
| 5,432,459 | A | 7/1995 | Thompson |
| 5,433,739 | A | 7/1995 | Sluijter et al. |
| 5,434,398 | A | 7/1995 | Goldberg |
| 5,436,566 | A | 7/1995 | Thompson |
| 5,438,302 | A | 8/1995 | Goble |
| 5,443,462 | A * | 8/1995 | Hannant ........................ 606/34 |
| 5,443,463 | A | 8/1995 | Stern et al. |
| 5,445,635 | A | 8/1995 | Denen |
| 5,451,224 | A | 9/1995 | Goble et al. |
| 5,458,597 | A | 10/1995 | Edwards et al. |
| 5,462,521 | A | 10/1995 | Brucker et al. |
| 5,472,441 | A | 12/1995 | Edwards et al. |
| 5,472,443 | A | 12/1995 | Cordis et al. |
| 5,478,303 | A | 12/1995 | Folry-Nolan et al. |
| 5,480,399 | A | 1/1996 | Hebborn |
| 5,483,952 | A | 1/1996 | Aranyi |
| 5,490,850 | A | 2/1996 | Ellman et al. |
| 5,496,312 | A | 3/1996 | Klicek |
| 5,496,313 | A | 3/1996 | Gentelia et al. |
| 5,500,012 | A | 3/1996 | Brucker et al. |
| 5,500,616 | A | 3/1996 | Ochi |
| 5,514,129 | A | 5/1996 | Smith |
| 5,520,684 | A | 5/1996 | Imran |
| 5,531,774 | A | 7/1996 | Schulman et al. |
| 5,534,018 | A | 7/1996 | Wahlstrand et al. |
| 5,536,267 | A | 7/1996 | Edwards et al. |
| 5,540,681 | A | 7/1996 | Strul et al. |
| 5,540,683 | A | 7/1996 | Ichikawa |
| 5,540,684 | A | 7/1996 | Hassler, Jr. |
| 5,540,724 | A | 7/1996 | Cox |
| 5,556,396 | A | 9/1996 | Cohen et al. |
| 5,558,671 | A | 9/1996 | Yates |
| 5,569,242 | A | 10/1996 | Lax et al. |
| 5,571,147 | A | 11/1996 | Sluijter et al. |
| 5,573,533 | A | 11/1996 | Strul |
| 5,584,830 | A | 12/1996 | Ladd et al. |
| 5,588,432 | A | 12/1996 | Crowley |
| 5,594,636 | A | 1/1997 | Schauder |
| 5,596,466 | A | 1/1997 | Ochi |
| 5,599,344 | A | 2/1997 | Paterson |
| 5,599,345 | A | 2/1997 | Edwards et al. |
| 5,599,348 | A | 2/1997 | Gentelia et al. |
| 5,605,150 | A | 2/1997 | Radons et al. |
| 5,613,966 | A | 3/1997 | Makower et al. |
| 5,613,996 | A | 3/1997 | Lindsay |
| 5,625,370 | A | 4/1997 | D'Hont |
| 5,626,575 | A | 5/1997 | Crenner |
| 5,628,745 | A | 5/1997 | Bek |
| 5,643,330 | A | 7/1997 | Holsheimer et al. |

| | | | | | |
|---|---|---|---|---|---|
| 5,647,869 A | 7/1997 | Goble et al. | 6,063,075 A | 5/2000 | Mihori |
| 5,647,871 A | 7/1997 | Levine et al. | 6,063,078 A | 5/2000 | Wittkampf |
| 5,651,780 A | 7/1997 | Jackson et al. | 6,068,627 A | 5/2000 | Orszulak et al. |
| 5,658,322 A | 8/1997 | Fleming | 6,074,386 A | 6/2000 | Goble et al. |
| 5,660,567 A | 8/1997 | Nierlich et al. | 6,074,388 A | 6/2000 | Tockweiler et al. |
| 5,674,217 A | 10/1997 | Wahlstrom et al. | 6,080,149 A | 6/2000 | Huang et al. |
| 5,685,840 A | 11/1997 | Schechter et al. | 6,093,186 A | 7/2000 | Goble |
| 5,688,267 A | 11/1997 | Panescu et al. | 6,102,497 A | 8/2000 | Ehr et al. |
| 5,690,692 A | 11/1997 | Fleming | RE36,871 E | 9/2000 | Epstein |
| 5,693,042 A | 12/1997 | Bioarski et al. | 6,113,591 A | 9/2000 | Whayne et al. |
| 5,694,304 A | 12/1997 | Telefus et al. | 6,113,596 A | 9/2000 | Hooven |
| 5,695,494 A | 12/1997 | Becker | 6,123,702 A | 9/2000 | Swanson et al. |
| 5,696,351 A | 12/1997 | Benn et al. | 6,132,429 A | 10/2000 | Baker |
| 5,696,441 A | 12/1997 | Mak et al. | 6,142,992 A | 11/2000 | Cheng et al. |
| 5,702,386 A | 12/1997 | Stern et al. | 6,155,975 A | 12/2000 | Urich et al. |
| 5,702,429 A | 12/1997 | King | 6,162,217 A | 12/2000 | Kannenberg et al. |
| 5,707,369 A | 1/1998 | Vaitekunas et al. | 6,171,304 B1 | 1/2001 | Netherly et al. |
| 5,712,772 A | 1/1998 | Telefus et al. | 6,188,211 B1 | 2/2001 | Rincon-Mora et al. |
| 5,713,896 A | 2/1998 | Nardella | 6,203,541 B1 | 3/2001 | Keppel |
| 5,718,246 A | 2/1998 | Vona | 6,210,403 B1 | 4/2001 | Klicek |
| 5,720,744 A | 2/1998 | Eggleston et al. | 6,222,356 B1 | 4/2001 | Taghizadeh-Kaschani |
| 5,722,975 A | 3/1998 | Edwards et al. | 6,228,080 B1 | 5/2001 | Gines |
| 5,729,448 A | 3/1998 | Haynie et al. | 6,228,081 B1 | 5/2001 | Goble |
| 5,733,281 A | 3/1998 | Nardella | 6,231,569 B1 | 5/2001 | Bek |
| 5,749,869 A | 5/1998 | Lindenmeier et al. | 6,235,020 B1 | 5/2001 | Cheng et al. |
| 5,749,871 A | 5/1998 | Hood et al. | 6,238,387 B1 | 5/2001 | Miller, III |
| 5,755,715 A | 5/1998 | Stern | 6,238,388 B1 | 5/2001 | Ellman |
| 5,766,165 A | 6/1998 | Gentelia et al. | 6,241,725 B1 | 6/2001 | Cosman |
| 5,769,847 A | 6/1998 | Panescu | 6,245,065 B1 | 6/2001 | Panescu |
| 5,772,659 A | 6/1998 | Becker et al. | 6,246,912 B1 | 6/2001 | Sluijter et al. |
| 5,792,138 A | 8/1998 | Shipp | 6,251,106 B1 | 6/2001 | Becker et al. |
| 5,797,802 A | 8/1998 | Nowak et al. | 6,258,085 B1 | 7/2001 | Eggleston |
| 5,797,902 A | 8/1998 | Netherly | 6,261,285 B1 | 7/2001 | Novak |
| 5,814,092 A | 9/1998 | King | 6,261,286 B1 | 7/2001 | Goble et al. |
| 5,817,093 A | 10/1998 | Williamson, IV et al. | 6,273,886 B1 | 8/2001 | Edwards |
| 5,820,568 A | 10/1998 | Willis | 6,275,786 B1 | 8/2001 | Daners |
| 5,827,271 A | 10/1998 | Buysse et al. | 6,293,941 B1 | 9/2001 | Strul |
| 5,830,212 A | 11/1998 | Cartmell | 6,293,942 B1 | 9/2001 | Goble et al. |
| 5,836,909 A | 11/1998 | Cosmescu | 6,296,636 B1 | 10/2001 | Cheng et al. |
| 5,836,943 A | 11/1998 | Miller, III | 6,306,131 B1 | 10/2001 | Hareyama et al. |
| 5,836,990 A | 11/1998 | Li | 6,306,134 B1 | 10/2001 | Goble et al. |
| 5,846,236 A | 12/1998 | Lindenmeier et al. | 6,309,386 B1 | 10/2001 | Bek |
| 5,868,737 A | 2/1999 | Taylor et al. | 6,325,799 B1 | 12/2001 | Goble |
| 5,868,739 A | 2/1999 | Lindenmeier et al. | 6,337,998 B1 | 1/2002 | Behl et al. |
| 5,868,740 A | 2/1999 | LeVeen et al. | 6,338,657 B1 | 1/2002 | Harper et al. |
| 5,871,481 A | 2/1999 | Kannenberg et al. | 6,350,262 B1 | 2/2002 | Ashley |
| 5,897,552 A | 4/1999 | Edwards et al. | 6,358,245 B1 | 3/2002 | Edwards |
| 5,908,444 A | 6/1999 | Azure | 6,364,877 B1 | 4/2002 | Goble et al. |
| 5,913,882 A | 6/1999 | King | 6,383,183 B1 | 5/2002 | Sekino et al. |
| 5,921,982 A | 7/1999 | Lesh et al. | 6,391,024 B1 | 5/2002 | Sun et al. |
| 5,925,070 A | 7/1999 | King et al. | 6,398,779 B1 | 6/2002 | Buysse et al. |
| 5,931,836 A | 8/1999 | Hatta et al. | 6,398,781 B1 | 6/2002 | Goble et al. |
| 5,935,124 A * | 8/1999 | Klumb et al. ............... 606/42 | 6,402,741 B1 | 6/2002 | Keppel et al. |
| 5,938,690 A | 8/1999 | Law et al. | 6,402,743 B1 | 6/2002 | Orszulak et al. |
| 5,948,007 A | 9/1999 | Starkebaum et al. | 6,416,509 B1 | 7/2002 | Goble et al. |
| 5,951,545 A | 9/1999 | Schilling et al. | 6,436,096 B1 | 8/2002 | Hareyama |
| 5,951,546 A | 9/1999 | Lorentzen | 6,451,015 B1 | 9/2002 | Rittman, III et al. |
| 5,954,686 A | 9/1999 | Garito et al. | 6,458,121 B1 | 10/2002 | Rosenstock |
| 5,954,717 A | 9/1999 | Behl et al. | 6,464,689 B1 | 10/2002 | Qin |
| 5,954,719 A | 9/1999 | Chen et al. | 6,464,696 B1 | 10/2002 | Oyama |
| 5,961,344 A | 10/1999 | Rosales et al. | 6,498,466 B1 | 12/2002 | Edwards |
| 5,971,980 A | 10/1999 | Sherman | 6,506,189 B1 | 1/2003 | Rittman, III et al. |
| 5,976,128 A | 11/1999 | Schilling et al. | 6,508,815 B1 | 1/2003 | Strul |
| 5,983,141 A | 11/1999 | Sluijter et al. | 6,511,476 B2 | 1/2003 | Hareyama |
| 6,010,499 A | 1/2000 | Cobb | 6,511,478 B1 | 1/2003 | Burnside et al. |
| 6,014,581 A | 1/2000 | Whayne et al. | 6,517,538 B1 | 2/2003 | Jacob et al. |
| 6,033,399 A | 3/2000 | Gines | 6,524,308 B1 | 2/2003 | Muller et al. |
| 6,044,283 A | 3/2000 | Fein et al. | 6,547,786 B1 | 4/2003 | Goble |
| 6,053,910 A | 4/2000 | Fleenor | 6,558,376 B2 | 5/2003 | Bishop |
| 6,053,912 A | 4/2000 | Panescu et al. | 6,560,470 B1 | 5/2003 | Pologe |
| 6,055,458 A | 4/2000 | Cochran et al. | 6,562,037 B2 | 5/2003 | Paton |
| 6,056,745 A | 5/2000 | Panescu et al. | 6,565,559 B2 | 5/2003 | Eggleston |
| 6,056,746 A | 5/2000 | Goble et al. | 6,573,248 B2 | 6/2003 | Ramasamy et al. |

| | | |
|---|---|---|
| 6,575,969 B1 | 6/2003 | Rittman, III et al. |
| 6,582,427 B1 | 6/2003 | Goble et al. |
| 6,620,157 B1 | 9/2003 | Dabney et al. |
| 6,623,423 B2 | 9/2003 | Sakurai |
| 6,629,973 B1 | 10/2003 | Wardell et al. |
| 6,635,057 B2 | 10/2003 | Harano |
| 6,645,198 B1 | 11/2003 | Bommannan et al. |
| 6,648,883 B2 | 11/2003 | Francischelli |
| 6,652,514 B2 | 11/2003 | Ellman |
| 6,663,623 B1 | 12/2003 | Oyama |
| 6,663,624 B2 | 12/2003 | Edwards |
| 6,666,860 B1 | 12/2003 | Takahashi |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,712,813 B2 | 3/2004 | Ellman |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,755,825 B2 | 6/2004 | Shoenman et al. |
| 6,758,846 B2 | 7/2004 | Goble et al. |
| 6,783,523 B2 | 8/2004 | Qin |
| 6,786,905 B2 | 9/2004 | Swanson et al. |
| 6,790,206 B2 | 9/2004 | Panescu |
| 6,796,981 B2 | 9/2004 | Wham |
| 6,824,539 B2 | 11/2004 | Novak |
| 6,830,569 B2 | 12/2004 | Thompson |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,893,435 B2 | 5/2005 | Roane |
| 6,923,804 B2 | 8/2005 | Eggers et al. |
| 6,929,641 B2 | 8/2005 | Goble et al. |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,966,907 B2 | 11/2005 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,381 B2 | 2/2006 | Harano et al. |
| 7,004,174 B2 | 2/2006 | Eggers et al. |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 * | 5/2006 | Reuss et al. ................. 600/300 |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,122,031 B2 | 10/2006 | Edwards et al. |
| 7,131,860 B2 | 11/2006 | Sartor et al. |
| 7,137,980 B2 | 11/2006 | Buysse et al. |
| 7,147,638 B2 | 12/2006 | Chapman et al. |
| 7,160,293 B2 | 1/2007 | Sturm et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,211,081 B2 | 5/2007 | Goble |
| 7,214,224 B2 | 5/2007 | Goble |
| 7,220,260 B2 | 5/2007 | Fleming et al. |
| 7,247,155 B2 | 7/2007 | Hoey et al. |
| 7,250,746 B2 | 7/2007 | Oswald et al. |
| 7,255,694 B2 | 8/2007 | Keppel |
| 7,282,048 B2 | 10/2007 | Goble et al. |
| 7,300,435 B2 | 11/2007 | Wham et al. |
| 7,303,557 B2 | 12/2007 | Wham et al. |
| 7,364,577 B2 | 4/2008 | Wham et al. |
| 7,367,972 B2 | 5/2008 | Francischelli et al. |
| RE40,388 E | 6/2008 | Gines |
| 7,396,336 B2 | 7/2008 | Orszulak et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |

| Publication No. | Date | Inventor |
|---|---|---|
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 A1 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1645235 | 4/2006 |
| EP | 0880220 B1 | 6/2006 |
| EP | 1707143 | 10/2006 |
| EP | 1810628 | 7/2007 |
| EP | 1810630 | 7/2007 |
| EP | 1810633 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO02/11634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO2004/103156 | 12/2004 |
| WO | WO2005048809 A1 | 6/2005 |
| WO | WO2005/060849 | 7/2005 |

OTHER PUBLICATIONS

International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2;(Mar. 2005); 160-164.
Medtrex Brochure "The O.R. Pro 300" 1 p. Sep. 1998.
Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J. Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.

International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedance" Am. J. Ml, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p.
Ogden Goertzel Alternative to the Fourier Transform: Jun. 1993 pp. 485-487 Electronics World; Reed Business Publishing, Sutton, Surrey, BG vol. 99, No. 9, 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp.
International Search Report PCT/US03/37110.
International Search Report PCT/US03/37310.
International Search Report EP 04009964.
International Search Report EP 98300964.6.
International Search Report EP 04015981.6.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search report EP 07008207.8 dated Sep. 5, 2007.
International Search Report EP 07010673.7 dated Sep. 24, 2007.

* cited by examiner

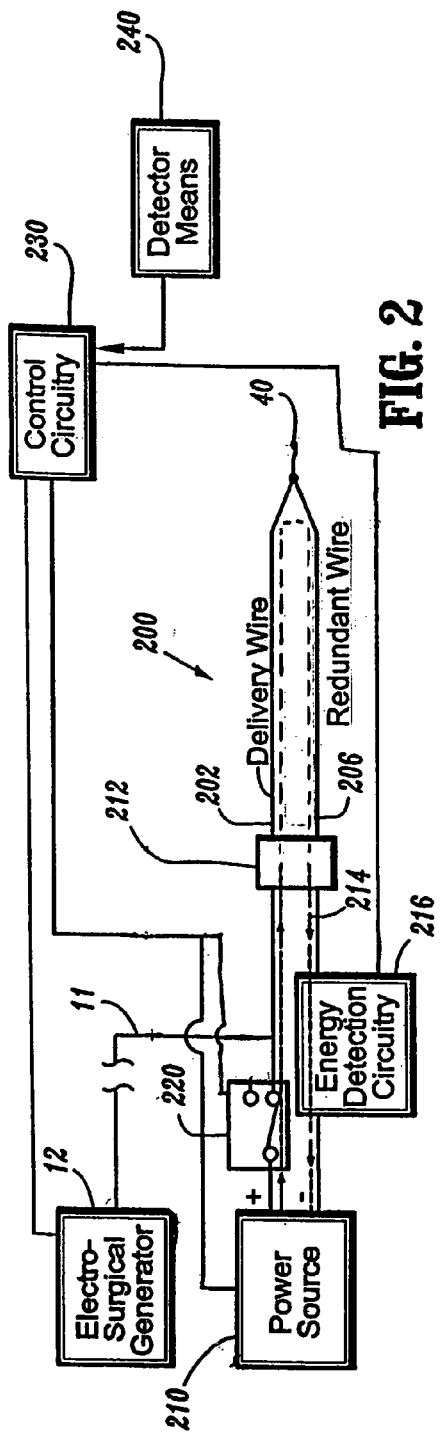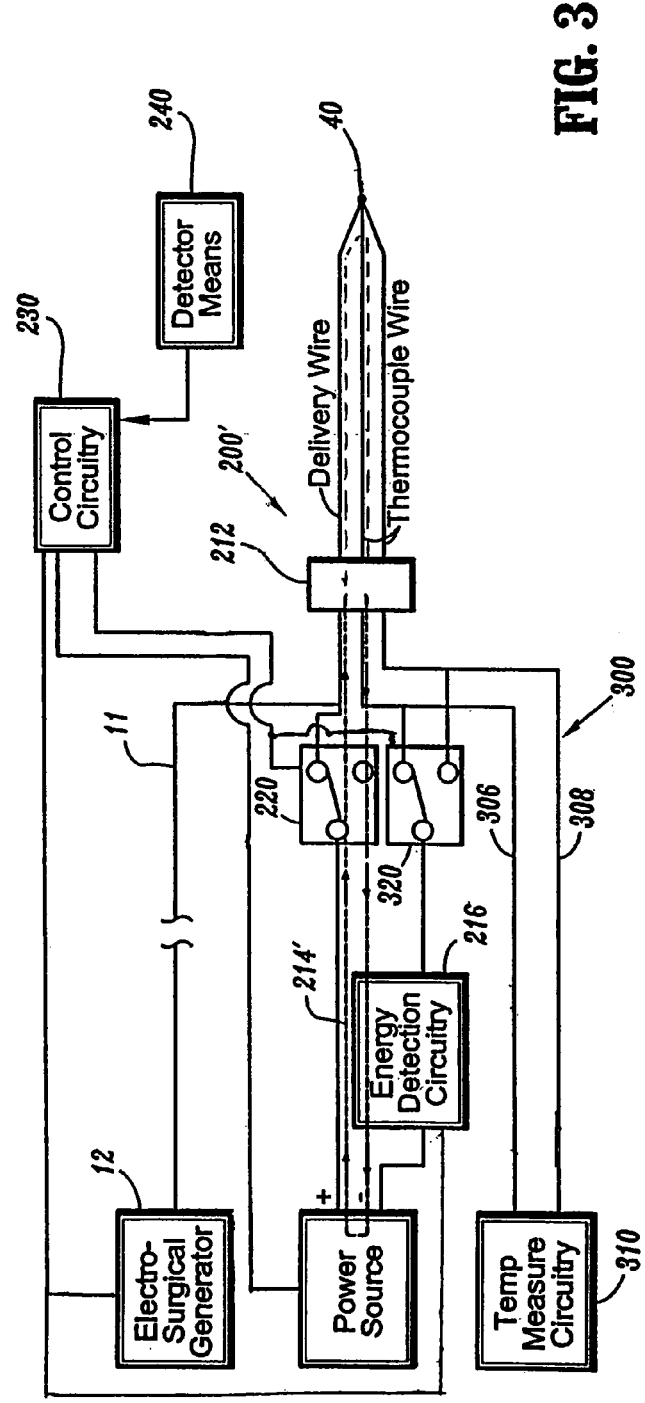
FIG. 2
FIG. 3

METHOD AND SYSTEM FOR CONTINUITY TESTING OF MEDICAL ELECTRODES

PRIORITY

This application claims priority to an application entitled "METHOD AND SYSTEM FOR CONTINUITY TESTING OF MEDICAL ELECTRODES", filed with the U.S. Patent and Trademark Office on Feb. 12, 2004, and assigned the Ser. No. 60/543,877, the contents of which are hereby incorporated by reference.

BACKGROUND

The present disclosure is directed to electrosurgical surgery and, in particular, to continuity testing of medical-surgical electrodes for continuity purposes.

TECHNICAL FIELD

Electrosurgical instruments have become widely used by surgeons in recent years. Accordingly, a need has developed for equipment and instruments which are easy to handle and operate, are reliable, and are safe in an operating environment. By and large, most electrosurgical instruments are hand-held instruments, e.g., an electrosurgical pencil, etc., which transfers radio-frequency (RF) electrical energy via a delivery electrode to a tissue site on a patient. The electrosurgical energy is returned to the electrosurgical source, e.g., an electrosurgical generator, via a return electrode, e.g., a pad positioned under a patient (i.e., a monopolar system configuration) or a smaller return electrode positioned in bodily contact with or immediately adjacent to the surgical site (i.e., a bipolar system configuration).

The particular waveforms produced by the RF source yield a predetermined electrosurgical effect, for example, coagulation, cauterization, cutting, blending, or sealing of body tissue. Coagulation is defined as a process of desiccating tissue wherein the tissue cells are ruptured and dehydrated/dried. Cauterization is defined as the use of heat to destroy tissue (also called "diathermy" or "electrodiathermy"). Cutting includes applying a high intensity electrical spark energy to tissue in order to produce a cutting, dissecting and/or dividing effect. Blending includes the function of cutting/dissecting combined with the production of a hemostasis effect. Sealing/hemostasis is defined as the process of liquefying the collagen and elastin in the tissue so that it reforms into a single fused mass with limited demarcation between opposite tissue walls.

On occasion, the electrode(s) (and the electrical connections related thereto) are subject to wear and tear and can fail, especially over time. Furthermore, the possibility exists that the electrodes and/or the electrical connections associated therewith may become damaged during manufacturing, assembly and/or handling. As a result thereof, the electrodes will not work as intended during use. Further, the surgeon does not know if the electrodes are functioning properly prior to initial use. Once a problem is identified and the electrode is fixed/replaced, the surgical procedure may be attempted again only after the operation field, the surgical team and the electrosurgical instrument are re-sterilized, thus causing delay, inconvenience and expense. Furthermore, in the event that the procedure to be performed is invasive, an unnecessary invasion was initially performed, introducing a risk of infection and discomfort and possibly the need for further anesthetics.

Electrosurgical instruments currently in use typically include external test discs for determining electrode continuity. The test disc is a metal disk that is connected to a return path from the delivery electrode. The operator of the electrosurgical device maneuvers the test disc to make electrical contact with the electrode forming a closed loop for an electrical path. A sensor provided in the test disc senses the presence of electrical energy. An indicator provided in the test disc indicates continuity status.

Since a test disc makes contact with the delivery electrode, it must be in a sterile condition, which typically complicates the sterilization procedure and subjects the test disc to stresses that may reduce the lifetime of the test disc. Furthermore, the operator is responsible for physically maneuvering the test disc for performing the continuity test, and for monitoring the outcome of the test, further taxing the operator and introducing the possibility of human error.

It would therefore be desirable to provide a technique to test the continuity of the electrodes of an electrosurgical device prior to activation and between uses. It would also be desirable to test the continuity of the electrodes during use to determine electrical effect and to assess electrode efficiency.

SUMMARY

An electrode continuity testing system and method for an electrosurgical system are provided. According to an aspect of the present disclosure, a continuity test circuit assembly is provided for testing electrical continuity between an electrosurgical generator generating electrosurgical energy and an electrode of an electrosurgical instrument, where the electrode is for receiving the electrosurgical energy and delivering the electrosurgical energy to tissue. The continuity test circuit assembly includes a first conductor coupling the electrode to the electrosurgical generator, at least one second conductor in electrical communication with a test power source providing electrical test energy and with the electrode for forming a test path. Energy detection circuitry is positioned along the test path for detecting the flow of the test energy through the test path for determining continuity status. Switching circuitry is positioned along the test path for selectively closing the test path for enabling a flow of test energy through the test path. A control module is provided for controlling the switching circuitry for controlling flow of the test energy through the test path.

According to another aspect of the disclosure, an electrosurgical generator for generating electrosurgical energy is provided. The electrosurgical energy is provided to an electrosurgical instrument having at least one electrode for delivery of the electrosurgical energy to tissue, the electrosurgical generator includes a continuity test circuit assembly for testing electrical continuity between the electrosurgical generator and an electrode of the at least one electrode of the electrosurgical instrument. The continuity test circuit assembly includes a test power source providing electrical test energy to a first conductor which is in electrical communication with the electrode and the electrosurgical generator and to at least one second conductor which is coupled to the first conductor for providing a path for current to flow between the first conductor and the at least one second conductor for establishing a test path through which the test energy flows between the first conductor and at least one conductor of the at least one second conductor. Energy detection circuitry is positioned along the test path for detecting the flow of the test energy through the test path for determining electrical continuity through the electrode.

In a further aspect of the present disclosure, a method is provided for testing continuity between an electrosurgical generator generating electrosurgical energy and an electrode, where the electrode receives the electrosurgical energy and delivers the electrosurgical energy to tissue. The method includes the steps of applying a test energy to a first conductor and at least one second conductor, wherein the first conductor is coupled between the electrosurgical generator and the electrode; coupling the at least one second conductor to the first conductor for providing a path for current to flow between the first conductor and the at least one second conductor for establishing a test path through which the test energy flows between the first conductor and at least one of the at least one second conductor. The method further includes the steps of detecting a flow of electrical test energy along the test path, the flow being indicative of continuity status; and selectively opening the test path for disrupting the flow of the test energy along the test path.

BRIEF DESCRIPTION OF THE DRAWINGS

Various embodiments will be described herein below with reference to the drawings wherein:

FIG. 2 is a schematic block diagram of components of the electrosurgical system shown in FIG. 1 relating to energy delivery, including a first embodiment of a continuity test circuitry;

FIG. 3 is a schematic block diagram of components of the electrosurgical system shown in FIG. 1 relating to energy delivery, including a second embodiment of a continuity test circuitry;

DETAILED DESCRIPTION

Figure 1:
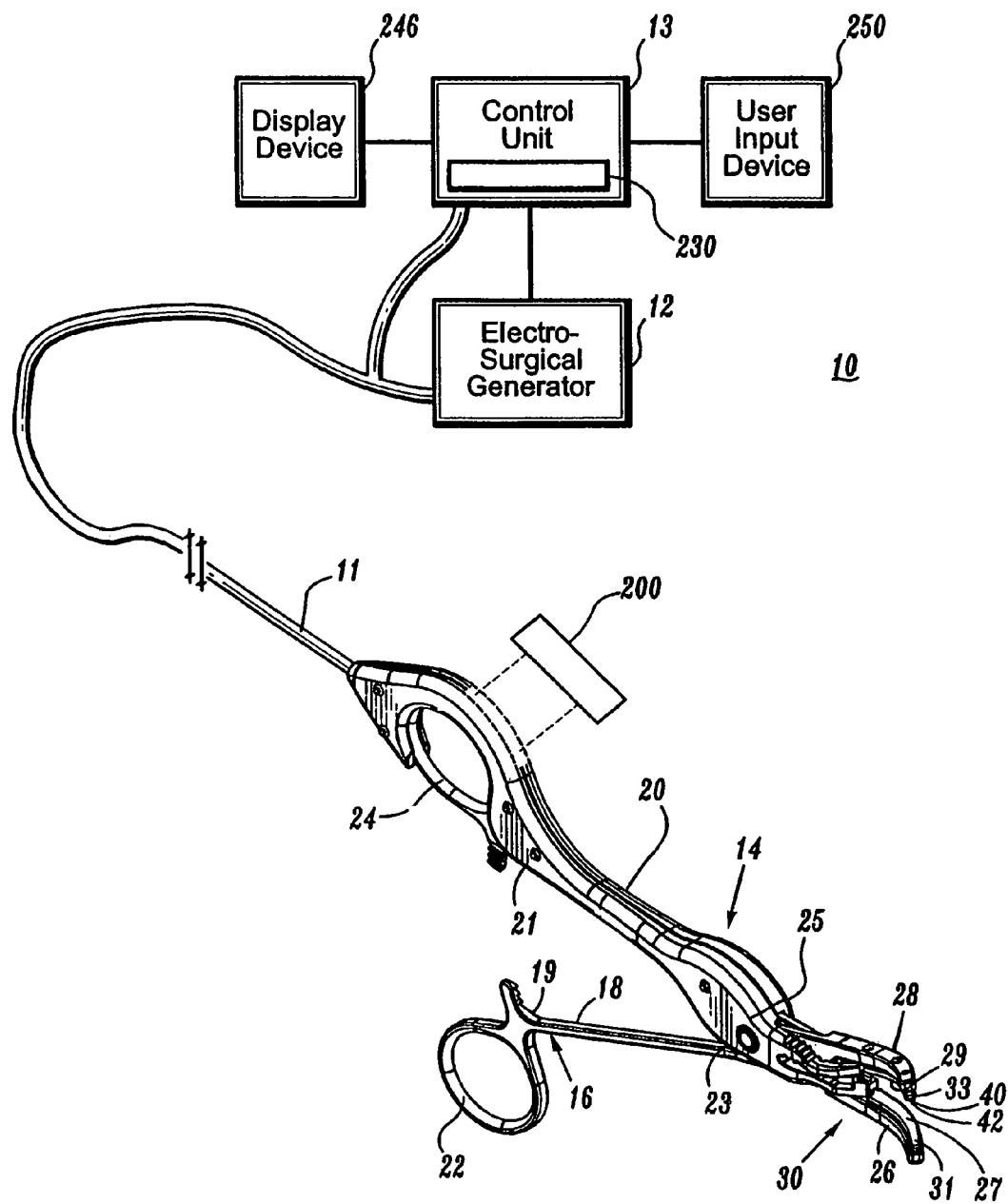
FIG. 1 is a schematic diagram of an electrosurgical system according to the present disclosure.

Preferred embodiments of the presently disclosed electrosurgical system will now be described in detail with reference to the drawing figures, where like reference numerals refer to similar or identical elements throughout the various figures. Referring to FIG. 1, there is shown a schematic diagram of one embodiment of the presently disclosed electrosurgical system, designated generally by referenced numeral 10, for use with open and/or laparoscopic surgical procedures.

The electrosurgical system 10 includes an electrosurgical generator 12 that generates electrosurgical energy, and provides the electrosurgical energy via connector 11 (e.g., a cable) to an exemplary electrosurgical instrument 14, shown in FIG. 1 as electrosurgical bipolar forceps. It is envisioned that the features and concepts (or portions thereof) of the present disclosure can be applied to any electrosurgical type of instrument, including monopolar or bipolar, e.g., pencil, suction coagulator, vessel sealer, etc. In the drawings and in the description which follows, the term "proximal", as is traditional, will refer to the end of the instrument 14 which is closer to the operator, while the term "distal" will refer to the end which is further from the operator. A control unit 13 is provided for controlling aspects of the electrosurgical generator 12 and/or the electrosurgical instrument 14. It is to be appreciated that the generator 12 and control 13 may be disposed in a single housing.

The instrument 14 includes forceps 16, including a pair of elongated shafts 18, 20 affixed to one another at a pivot point.

Each shaft 18, 20 includes a proximal end 19 and 21 and a distal end 23 and 25, respectively. The proximal end 19, 21 of each shaft 18, 20 is provided with a handle member 22, 24, respectively, attached thereto to allow the operator to effect movement of at least one of the shafts 18, 20 relative to one another. Extending from the distal end 23, 25 of each shaft 18, 20 are end effectors 26, 28, respectively. The end effectors 26, 28 are movable relative to one another in response to movement of handle members 22 and 24. In embodiments in which the instrument 14 is monopolar there is one end effector.

An electrode assembly 30 is provided including delivery electrode 33, where a return electrode 31 and the delivery electrode 33 are provided at respective inner facing surfaces 27, 29 of respective distal ends 23, 25 of respective shafts 18, 20. It is envisioned that in other embodiments the electrodes 31, 33 may be positioned on strategically selected surface(s) of the one or more end effectors in accordance with the application. For monopolar embodiments, a return electrode assembly is typically placed at a convenient place on the patient's body and is attached to the generator by a conductive material. The electrodes 31, 33 include electrodes selected from a variety of electrodes, such as, "snare", "blade", "loop", "needle" and/or "ball" electrodes.

The delivery electrode 33 delivers the electrosurgical energy to the patient at a delivery point 40, e.g., the point on the electrode assembly 30 that contacts the patient, of a contact surface 42 of the delivery electrode 33 which is formed of a conductive material. The configuration of the contact surface 42 may be selected from a variety of configurations, in accordance with the variety of electrode used and the surgical application being performed. A schematic representation of internal continuity test circuitry 200 is shown in a cut away and exploded portion of electrode assembly 30 for testing continuity between the delivery electrode 33 and the electrosurgical generator 12 for assuring proper delivery of electrosurgical energy to the delivery point 40. The continuity test circuitry 200 may be positioned at various locations, including in the electrosurgical generator 12 or in the electrosurgical instrument 14 (e.g., near a proximal or distal end of the electrosurgical instrument 14, along the end effector 28, etc.) or a combination thereof. In a preferred embodiment, the continuity test circuitry 200 is positioned in the electrosurgical generator 12 to verify the electrical continuity from the generator 12 to the electrosurgical instrument in addition to testing the continuity of the generator 12 to the delivery electrode 33.

FIG. 2 schematically shows components of the electrosurgical system 10 related to delivery of electrosurgical energy, continuity testing and control thereof, including a first embodiment of the continuity test circuitry 200. A portion of the continuity test circuitry 200 may be integrated within the electrode assembly 30. Electrosurgical energy is conducted via a delivery wire 202 to delivery point 40 of an electrode of the electrode assembly 30. The electrode assembly 30 is preferably disposed within a housing of the electrosurgical instrument 14, where the delivery point 40 is exposed from the housing.

The continuity test circuitry 200 may be configured to test any conductor of a variety of conductors that may be included in the electrode assembly 30. In the embodiment shown, the continuity test circuitry 200 is configured to test the delivery wire 202 at a point close to the delivery point 40 or at the delivery point 40. At least one redundant wire 206 (e.g., an additional wire for forming the test circuit) is provided, where the redundant wire 206 is connected to the delivery wire 202 at or near the delivery point 40. In an electrode assembly which is provided with at least one additional wire that connects to the delivery wire at or near the delivery point 40, at least one of the at least one additional wire may be used instead of the redundant wire 206, such as in the embodiment described below with reference to FIG. 3.

The continuity test circuitry 200 preferably includes a test power source 210, coupling circuitry 212, and energy detection circuitry 216. The delivery wire 202 (e.g., a first conductor) and the at least one redundant wire 206 (e.g., a second conductor) are coupled to the test circuitry. The delivery wire 202 and redundant wire 206 each include conduits for propagating electrical energy, including, but not limited to, metal conductive wires. Voltage is applied across the delivery wire 202 and the redundant wire 206 by the test power source 210, so that when continuity exists current flows through the delivery wire 202 and the redundant wire 206 via a closed test path 214. Detection of the current flow indicates continuity. The test path 214 is shown by dotted lines representing a conceptual path followed by the test energy as the test energy flows through the physical components of the continuity test circuitry 200. The energy detection circuitry 216 detects the flow of the test energy along the test path 214.

The continuity test circuitry 200 may optionally further include switching circuitry 220 for selectively opening the test path 214. Furthermore, the continuity test circuitry 200 may optionally be controlled by a control module 230 for controlling the flow of the test energy in accordance with a predetermined condition.

The test power source 210 which generates the test energy may be a direct current source or an alternating current source. The test power source 210 is preferably a battery sized for integration into the electrosurgical generator 12 or the electrosurgical instrument 14. Alternatively, the test power source 210 may be an AC or DC source provided externally from the continuity test circuitry 200, such as a power source providing power to another system. Connectors may be provided for electrically connecting the test power source 210 to the continuity test circuitry 200. The test energy provided by the test power source 210 is preferably a low voltage, where the voltage is sufficiently high enough for detection when the test path 214 is closed, yet is minimized for reducing power consumption and the generation of undesirable entities such as noise or heat. It is preferable that the test energy is substantially lower than the energy generated by the electrosurgical generator 12.

The coupling circuitry 212 is preferably located at or close to the delivery point 40 and may include an electrical connector for providing an electrical path between the delivery wire 202 and the generator 12 and between the redundant wire 206 and the generator 12.

The energy detection circuitry 216 includes circuitry capable of detecting electrical energy, such as a current detector or voltage detector and outputting a result signal indicative of sensed energy. The energy detection circuitry 216 is placed at a point along the test path 214, and preferably is not connected directly to the delivery wire 202 for not placing a load on the delivery wire 202 during a surgical procedure. It is preferable for the energy detection circuitry 216 to be placed in or near the electrosurgical generator 12.

The energy detection circuitry 216, which may include an optocoupler or other coupling means, is preferably coupled to the redundant wire 206 for detecting the current flow along the redundant wire 206, while providing electrical isolation between circuitry for delivering electrosurgical energy (e.g., circuitry that is in patient contact) and the test energy. The optocoupler includes Light Emitting Diode (LED) circuitry for sensing and converting test energy flowing through the redundant wire 206 (preferably electrical energy) into light energy and photo detector circuitry spaced from and aligned with the LED circuitry for detecting light emitted from the LED circuitry and generating the result signal indicative of energy sensed.

During a continuity test, the result signal indicates the outcome of the continuity test. Preferably, the result signal is provided to at least one indicator provided with the electrode assembly 30, the electrosurgical instrument 14, the electrosurgical generator 12 and/or the control unit 13, such as at least one display device 246, at least one indicator light and/or an audio indicator for indicating the status of the continuity test to a user, particularly when the continuity test has failed. Furthermore, the result signal may be provided to the control module 230.

The switching circuitry 220 is provided along the test path 214 for selectively opening the test path 214 so that the test energy does not flow throughout the test path 214, and particularly so that the test energy does not flow when a continuity test is not being performed. More specifically, the switching circuitry 220 opens the test path 214 during a surgical procedure so that test energy is not delivered to the patient, is not sensed or measured during the surgical procedure, and does not otherwise interfere with the procedure, and/or so that the continuity test circuitry 200 is not detecting energy during the surgical procedure. The present disclosure is not limited to opening the test path during a surgical procedure, and it is contemplated that the test energy may be permitted to flow during a surgical procedure; however it is expected that the generator 12 would be disabled during the continuity test.

The switching circuitry 220 may be strategically located in at least one location, such as along the delivery wire 202 for opening up the test path 214 along the delivery wire 202, as shown in FIG. 2, along the redundant wire 206 for opening up the test path 214 along the redundant wire 206, in the electrosurgical instrument 14, in the electrosurgical generator 12, included in the continuity test circuitry 200, included in the coupling circuitry for opening up the test path that flows through the coupling circuitry 212, included in the energy detection circuitry 216 for disabling detection of test energy, within the test power source 210 for discontinuing flow of the test energy into the continuity test circuitry 200 or any combination thereof. The switching circuitry 220 is preferably software controlled by the control module 230 in accordance with a predetermined condition (e.g., a user request, a sensed condition, a system generated request, etc.).

Control module 230 receives and processes an electrode present signal from a detector means 240, and/or a user or system generated request signal for initiating a continuity test, and generates an enable continuity test signal upon receipt thereof. Generation of the electrode present signal by the detector means 240 indicates that an electrode assembly 30 has been mounted on the electrosurgical instrument 14 or that an electrode has been coupled to the generator. The user request signal may be generated by user operation of a user input device 250, where the user input device may include one or more devices, such as a keyboard, button, etc., associated with and/or integrated into the electrosurgical generator 12, the electrosurgical instrument 14, control unit 13 and/or electrode assembly 30.

The control module 230 may control the electrosurgical generator 12, e.g., prevent generation of electrosurgical energy by the electrosurgical generator 12, upon receipt of an enable continuity test signal and/or throughout the continuity test (e.g., until a successful result signal is received by the control module 230). Furthermore, the control module 230 may receive and process the result signal generated by the energy detection circuitry 216, such as for generating a message to be displayed on the display device 246, and/or for controlling the electrosurgical generator 12, e.g., preventing generation of electrosurgical energy by the electrosurgical generator 12 when the result signal indicates a failure, etc.

It is further contemplated that the electrosurgical generator 12 and the test power source 210 are not referenced to the same point so that electrosurgical energy does not flow throughout the test path 214 during a surgical procedure or during a continuity test and the electrosurgical energy does not interfere with operation of the test power source 210. The electrosurgical energy follows a path different from the test path 214, in which the electrosurgical energy flows from the delivery electrode 33 to the return electrode 31. It follows that disablement of the electrosurgical generator 12 would not be required during a continuity test, however, it is expected that the generator 12 would be disabled during the continuity test.

It is contemplated that in addition to (or instead of) sensing initial mounting of the electrode assembly 30, other conditions may be sensed and corresponding signals generated for generating the enable continuity test signal for automatically performing a continuity test, such as termination of an electrosurgical procedure.

The control module 230 may include one or more software modules, each software module including a series of programmable instructions executable by at least one processor. The one or more software modules executable by the at least one processor include a continuity test enable software module, which receives and processes the electrode present signal and generates the enable continuity test signal as described below. The one or more software modules may further include a disable electrosurgical generator module, which receives and processes the result signal generated by the energy detection circuitry 216 and generates a disable signal which is provided to the electrosurgical generator 12 for preventing the electrosurgical generator 12 from generating electrosurgical energy when the continuity test fails. The control module 230 may include analog circuitry, logic circuitry, firmware, at least one processor of the at least one processor, etc., or a combination thereof. At least one processor of the at least one processors may be included in control unit 13 conventionally provided for controlling the electrosurgical generator and/or instrument.

The detector means 240 includes a sensor and/or circuitry for detecting the presence of mounted electrode assembly 30 and generating the electrode present signal. Detector means 240 may include, for example, a first electrical contact or equivalent that mates with a second electrical contact or equivalent provided on the electrode assembly 30. Circuitry is provided for transmitting the electrode present signal to the control unit 13. Information indicating the type of electrode assembly 30 mounted on the electrosurgical instrument may further be provided to the control module 230 for the control module 230 to configure the continuity test to be congruent with the configuration of the electrode assembly 30 presently mounted.

The enable continuity test signal enables the continuity test circuitry 200 to perform a continuity test. The enable continuity test signal may control operation of the test power source 210 and/or the switching circuitry 220. For example, when the continuity test signal does not enable the continuity test circuitry 200 to perform the continuity test (e.g., the continuity test signal is "low"), the test power source 210 is turned off and/or the switching circuitry 220 opens the test path 214 so that test energy does not flow, and when the continuity test signal enables the continuity test circuitry 200 to perform the continuity test (e.g., the continuity test signal is "high"), the test power source 210 is turned on and/or the switching circuitry 220 closes the test path 214 so that the test energy may flow through a closed path if the electrode is connected for proper continuity as required for proper application of electrosurgical energy.

In operation, upon mounting an electrode assembly 30 onto the electrosurgical instrument 14, the presence of the electrode assembly 30 is automatically sensed and an electrode present signal is generated by the detection means 240. The control module 230 generates a continuity test enable signal for enabling the continuity test circuitry 200 to perform a continuity test. Preferably, the continuity test is performed one time when the test is successful (e.g., result signal generated by the energy detection circuitry 216 is "high"), but is not limited thereto. When the continuity test fails (e.g., result signal generated by the energy detection circuitry 216 is "low"), the continuity test may be discontinued and a failure indication is provided to the user, or the continuity test may be continued until the continuity test is successful. Typically, the continuity test is discontinued before beginning an electrosurgical procedure. When performed automatically, the continuity test is transparent to the user unless the continuity test fails. The user is not burdened with administering, discontinuing or monitoring the results of the continuity test.

It is to be appreciated that the continuity test circuitry 200 is preferably disposed in or proximate the electrosurgical generator 12. In this embodiment, the test power source 210, coupling circuitry 212, energy detection circuitry 216 and switching circuitry 220 are all disposed in or on the electrosurgical generator 12. Optionally, the continuity test circuitry 200 may derive test power from an existing power source providing power to the electrosurgical generator 12, and thus, the test power source 210 may be eliminated. By positioning the continuity test circuitry 200 in the electrosurgical generator 12, continuity from the electrosurgical generator to the electrosurgical instrument will be verified in addition to testing the continuity of the conductor in the electrode assembly.

A detailed diagram of a second embodiment of the continuity test circuitry 200' is shown in FIG. 3. The electrode assembly 30 is further provided with additional circuitry, shown in this example as temperature sensing circuitry 300, including a pair of additional conductive wires 306, 308 (e.g., second conductors), configured as temperature sensors in the example shown, and more specifically as exemplary thermocouple wires, but not limited thereto, and temperature measuring circuitry 310 coupled to the thermocouple wires for measuring the temperature sensed by the thermocouple wires, the thermocouple measuring circuit 310 being preferably disposed in the generator 12. The additional circuitry is not limited to temperature sensing circuitry, and may include one or more additional conductive wires as well as other elements providing additional functions to the electrosurgical system 10, provided that the at least one of the one or more additional conductive wires may be included in the continuity test circuitry 200' for completing test path 214'.

Second switching circuitry 320 is provided along the additional conductive wires 306, 308 for selecting at least one, and preferably only one, of the additional conductive wires 306, 308 to be included in the test path 214' for testing electrical conductivity and/or thermocouple function of the selected additional conductive wire 306, 308 within the test path. As shown in FIG. 3, in a first position, the second switching circuitry 320 includes additional conductive wire 306 (but not 308) in the test path 214', and in a second position, the second switching circuitry 320 includes additional conductive wire 308 (but not 306) in the test path. The second switching circuitry 320 is not required as long as at least one of the one or more additional conductive wires is included in the test path 214'. Redundant wire 206 shown in FIG. 2 is not included, as the additional conductive wires 306, 308 perform the function of the second conductor provided by the redundant wire 206.

The control module 230 may generate control signals for controlling the second switching circuitry 320, such as for controlling which additional conductive wire 306 or 308 is selected to be included in the test path 214', such as by selecting the appropriate additional conductive wire in accordance with a predetermined condition (e.g., a user request, results of a previous continuity test, a system request, a sensed condition, etc.). For example, the control module 230 may test the additional conductive wires in sequence by sequencing to a subsequent additional conductive wire when a continuity test is completed on currently tested additional conductive wire. Results of the continuity tests may be provided to a user, such as via a display or a printout.

It is to be appreciated that by switching the second switching circuitry 320 from the first to second position during a continuity test, the selected wire of the thermocouple wires 306, 308 of temperature sensing circuitry 300 are also verified for continuity. In this embodiment, an additional indicator may be provided to alert the user of the thermocouple continuity.

Figure 4:
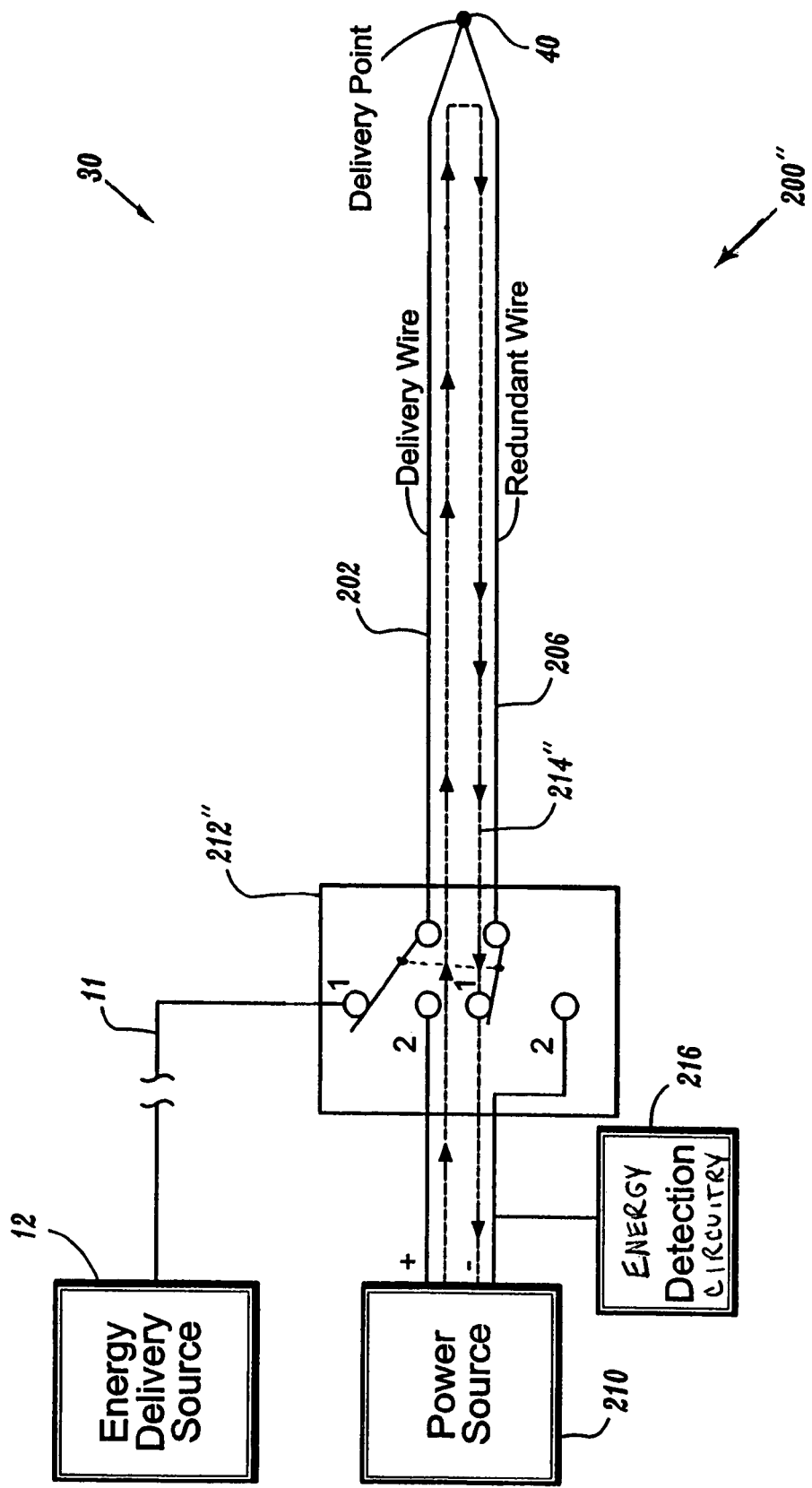
FIG. 4 is a schematic block diagram of components of the electrosurgical system shown in FIG. 1 relating to energy delivery, including a third embodiment of a continuity test circuitry.

A detailed diagram of a third embodiment of the continuity test circuitry 200" is shown in FIG. 4. In this embodiment, coupling circuitry 212" is provided for coupling the electrode assembly 30 to the generator 12 and includes switching circuitry for opening and closing the test path 214". The coupling circuitry 212" is operable for delivery of electrosurgical energy to the delivery wire 202 in a first position, and for forming a closed conceptual test path 214" between the delivery wire 202, redundant wire 206 and test power source 210 in a second position. In the first position of the coupling circuitry 212", the electrosurgical generator 12 is coupled to the delivery wire 202 for delivering electrosurgical energy to the delivery point 40. Furthermore, an end of the redundant wire 206 opposite the end coupled to the delivery wire 202 is decoupled, e.g., forming an open circuit, from the test power source 210, so as to avoid energy from the electrosurgical generator 12 being fed into the test power source 210. In this embodiment, the electrosurgical energy substantially does not interfere with performance of continuity tests, and the test energy substantially does not interfere with delivery of electrosurgical energy to the patient, even when the electrosurgical generator 12 and the test power source 10 are referenced to the same point, and/or are simultaneously enabled.

In the second position of the coupling circuitry 212", the delivery wire 202 is decoupled from the electrosurgical generator 12 and coupled to the test power source 210, and the redundant wire 206 is coupled to the test power source 210 for forming the test path 214". Preferably, the coupling circuitry 212" is a double-pole, double-throw relay. The control module 230 and detection means 240 may further be provided, such as for controlling the coupling circuitry 212" including selecting operation in the first or second position, such as in accordance with the enable continuity test signal or user requests. As described above, with reference to FIGS. 1-3, the control module 230 may provide further control functions, such as receiving signals, such as result signals from the energy detection circuitry 216 and/or user request signals, and/or providing control signals to the electrosurgical generator 12.

Figure 5:
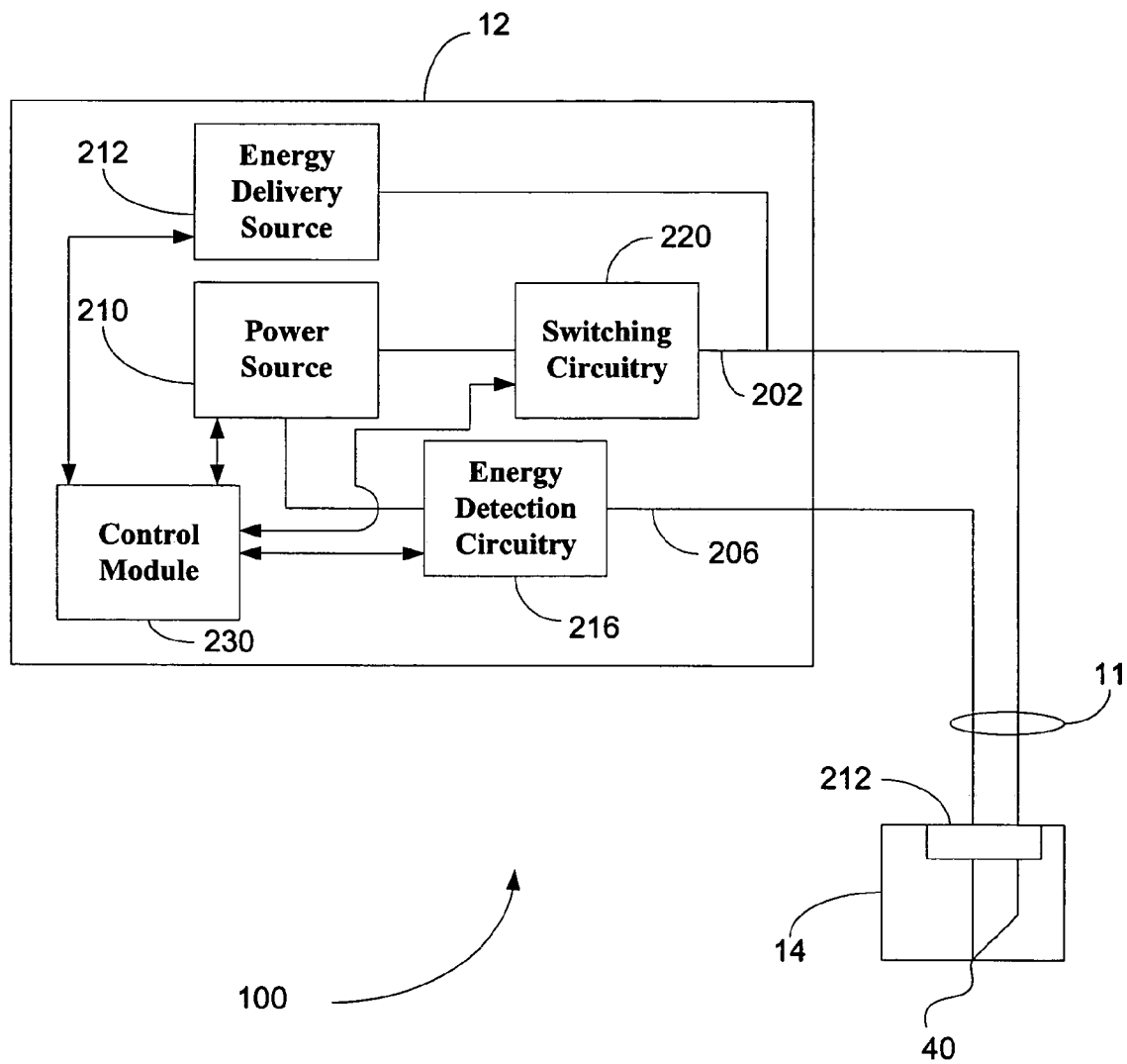
FIG. 5 is a block diagram of the electrosurgical system according to FIG. 1, having a preferred configuration of continuity test circuitry.

With respect to FIG. 5, an electrosurgical system 100 is shown having an exemplary configuration in which at least a portion of the continuity test circuitry 200 is included in the electrosurgical generator 12. The test power source 210, energy detection circuitry 216, and switching circuitry 220 are disposed within and/or integrated with the electrosurgical generator 12. The redundant wire 206 and the delivery wire 202 extend from the electrosurgical generator 12, through connector 11 and the electrosurgical instrument 14 to the coupling circuitry 212, which preferably positioned proximate the delivery point 40. The delivery wire 202 further extends to the delivery point 40 for delivering the electrosurgical energy to the patient via a delivery electrode (such as delivery electrode 33 of FIG. 1). A return electrode (not shown) is provided for providing a return path to the electrosurgical energy, where the return electrode may be provided in a bipolar or monopolar configuration. As described above with reference to FIGS. 1-4, the control module 230 may be in communication with the electrosurgical generator 12 and/or the components of the continuity test circuitry 200 for receiving signals, such as result signals from the energy detection circuitry 216 and/or user request signals, and/or for providing control signals, such as to the switching circuitry 220 and/or the electrosurgical generator 12.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A continuity test circuit assembly for testing electrical continuity between an electrosurgical generator generating electrosurgical energy and an electrode of at least one electrode of an electrosurgical instrument for receiving the electrosurgical energy and delivering the electrosurgical energy to tissue, the continuity test circuit assembly comprising:
   a first conductor coupling the electrode to the electrosurgical generator;
   at least one second conductor in electrical communication with a test power source and with the electrode for forming a test path, said test power source configured to selectively provide electrical test energy;
   energy detection circuitry positioned along the test path for detecting a flow of the test energy through the test path for determining continuity status;
   switching circuitry positioned along the test path for selectively closing or opening the test path for enabling the flow of the test energy through the test path;
   a control module configured to activate the switching circuitry to control the flow of the test energy through the test path; and
   a detector which detects at least one predetermined condition, and wherein the control module generates a signal to automatically activate the switching circuitry upon detection of the at least one predetermined condition by the detector such that the switching circuitry opens or closes the test path upon activation by the signal generated by the control module.

2. A continuity test circuit assembly according to claim 1, wherein the at least one predetermined condition which is detected includes mounting of the electrode on the electrosurgical instrument, and wherein the control module controls the switching circuitry to close the test path upon detection of the at least one predetermined condition.

3. A continuity test circuit assembly according to claim 1, wherein the at least one predetermined condition which is detected includes delivery of electrosurgical energy to the electrode, and wherein the control module controls the switching circuitry to open the test path upon detection of the at least one predetermined condition.

4. A continuity test circuit assembly according to claim 1, wherein the switching circuitry further selectively enables delivery of the electrosurgical energy to the tissue, and the control module controls the switching circuitry to open the test path upon detection of the at least one predetermined condition.

5. A continuity test circuit assembly according to claim 1, wherein the energy detection circuitry provides electrical isolation to the test energy via an optocoupler.

6. A continuity test circuit assembly according to claim 1, further comprising second switching circuitry for selecting one of the at least one second conductors to be included in the test path.

7. A continuity test circuit assembly according to claim 1, further comprising second switching circuitry for selecting one of the at least one second conductors to be included in the test path, wherein the control module controls the second switching circuitry at least partially in accordance with detection of the predetermined condition.

8. A continuity test circuit assembly according to claim 1, wherein the at least one second conductor includes at least a pair of thermocouple wires.

9. A continuity test circuit assembly according to claim 1, wherein the switching circuitry is provided along at least one of the first conductor, the at least one second conductor and the test power source.

10. A continuity test circuit assembly according to claim 1, wherein at least one of the test power source, the energy detection circuitry and the switching circuitry are disposed within the electrosurgical generator.

11. A continuity test circuit assembly according to claim 1, wherein the test power source derives power from a power source of the electrosurgical generator.

12. A continuity test circuit assembly according to claim 1, wherein the test energy provided by the test power source is substantially lower than the energy delivered by the electrosurgical generator.

13. An electrosurgical generator for generating electrosurgical energy which is provided to an electrosurgical instrument having at least one electrode for delivery of the electrosurgical energy to tissue, the electrosurgical generator comprising:
    a continuity test circuit assembly for testing electrical continuity between the electrosurgical generator and an electrode of the at least one electrode of the electrosurgical instrument, the continuity test circuit assembly comprising:
    a test power source configured to selectively provide electrical test energy to a first conductor which is in electrical communication with the electrode and the electrosurgical generator and to at least one second conductor which is coupled to the first conductor for providing a path for current to flow between the first conductor and the at least one second conductor for establishing a test path through which the test energy flows between the first conductor and at least one conductor of the at least one second conductor;
    energy detection circuitry positioned along the test path that detects a flow of the test energy through the test path for determining electrical continuity through the electrode;
    switching circuitry positioned along the test path that selectively opens or closes the test path thereby controlling the flow of test energy through the test path; and
    a control module that generates a signal to control the switching circuitry for automatically controlling flow of the test energy through the test path upon detection of at least one predetermined condition such that the signal generated by the control module causes the switching circuitry to open or close the test path.

14. An electrosurgical generator according to claim 13, wherein the at least one predetermined condition includes detection of mounting of the electrode on the electrosurgical instrument, and wherein the control module controls the switching circuitry to close the test path upon detection of the at least one predetermined condition.

15. An electrosurgical generator according to claim 13, wherein the at least one predetermined condition includes detection of delivery of the electrosurgical energy to the electrode, and wherein the control module controls the switching circuitry to open the test path upon detection of the at least one predetermined condition.

16. An electrosurgical generator according to claim 13, wherein the switching circuitry selectively enables delivery of the electrosurgical energy to the tissue, and the control module controls the switching circuitry to open the test path upon detection of the at least one predetermined condition.

17. An electrosurgical generator according to claim 13, wherein the energy detection circuitry provides electrical isolation to the test energy via an optocoupler.

18. An electrosurgical generator according to claim 13, wherein the continuity test circuit assembly further comprises second switching circuitry for selecting one of the at least one second conductors to be included in the test path.

19. An electrosurgical generator according to claim 13, wherein the continuity test circuit assembly further comprises second switching circuitry for selecting one of the at least one second conductors to be included in the test path, and the control module controls the switching circuitry at least partially in accordance with detection of the predetermined condition.

20. An electrosurgical generator according to claim 13, wherein the at least one second conductor includes at least a pair of thermocouple wires.

* * * * *